(12) United States Patent
Fernandez (10) Patent No.: US 9,579,259 B2
(45) Date of Patent: Feb. 28, 2017

(54) MEDICAMENT DISPENSING SYSTEM

(71) Applicant: Leopoldo Meneses Fernandez, Iztapalapa (MX)

(72) Inventor: Leopoldo Meneses Fernandez, Iztapalapa (MX)

(*) Notice: Subject to any disclaimer, the term of this patent is extended or adjusted under 35 U.S.C. 154(b) by 99 days.

(21) Appl. No.: 14/442,592

(22) PCT Filed: Nov. 15, 2013

(86) PCT No.: PCT/MX2013/000142
§ 371 (c)(1),
(2) Date: May 13, 2015

(87) PCT Pub. No.: WO2014/077670
PCT Pub. Date: May 22, 2014

(65) Prior Publication Data
US 2016/0287478 A1    Oct. 6, 2016

(30) Foreign Application Priority Data
Nov. 16, 2012    (MX) .................. MX/a/2012/013347

(51) Int. Cl.
*A61J 1/20* (2006.01)
*A61J 7/00* (2006.01)
*A61M 5/315* (2006.01)
*A61J 1/14* (2006.01)

(52) U.S. Cl.
CPC ........... *A61J 1/2096* (2013.01); *A61J 7/0053* (2013.01); *A61M 5/31513* (2013.01); *A61J 1/1443* (2013.01)

(58) Field of Classification Search
CPC ...... A61J 7/0053; A61J 1/2096; A61J 1/1443; A61J 1/20; A61M 5/31513
See application file for complete search history.

(56) References Cited

U.S. PATENT DOCUMENTS

| 5,137,511 A | 8/1992 | Reynolds |
| 5,893,397 A | 4/1999 | Peterson et al. |
| 8,016,798 B2 | 9/2011 | Sparks et al. |

FOREIGN PATENT DOCUMENTS

| ES | 2047546 T3 | 3/1994 |
| ES | 2200041 T3 | 1/2004 |
| ES | 2342717 T3 | 7/2010 |
| WO | 2012057845 A1 | 3/2012 |

*Primary Examiner* — Nathan R Price
*Assistant Examiner* — Melissa A Snyder
(74) *Attorney, Agent, or Firm* — Culhane Meadows PLLC; Kevin W. Grierson; J. Scott Anderson (57) ABSTRACT

A medicament dispensing system for orally dispensing medicament to a patient, wherein the system comprises in combination a syringe to extract medicament, an adapter to be inserted tightly into the medicament container and serve as an airtight inner cap thereof, as well as to serve as a guide for the syringe; and a housing or hood for containing and storing in a sterile manner said syringe and adapter.

13 Claims, 11 Drawing Sheets

MEDICAMENT DISPENSING SYSTEM

The present invention refers to a medicament dispensing system for dispensing medicament orally to a patient, in particular an infant or child, without spillage or contamination of the medicament by the direct introduction of the syringe into the vial. The present invention relates equally to a system for dispensing medicament comprising in combination a plunger, an inverted adapter and a piston designed to a thousandths of a millimeter level for dispensing the exact amount of medicament due to high-precision plunger, which does not require the inclusion of a cover of rubber or the like to bring the vacuum effect of perform the suction of the medicament, providing a completely airtight and leak-proof syringe, economical and easy to produce.

The dispensing syringe of the present invention can be manufactured in various capacities ranging from 3 ml to 10 ml, and using a variety of materials which are highly sterile and economical, which makes the syringe useful for a wide application of medicament dose.

BACKGROUND OF THE INVENTION

Currently, there is a great use of syringes and devices for dispensing medicament orally; however, all these devices have a variety of drawbacks when they are used. Firstly, most of these syringes should be introduced into the vial of medicament to suctioned it, causing with this the spillage of medicament and therefore the waste thereof, which causes invest more money to buy additional medicament to finish the treatment. Similarly, the introduction of said syringe promotes the contamination of the medicament when the syringe is used more than once, since commonly when the syringe is not in use, this is stored in the medicament box or in a bag or the like which are not sterile containers, causing that the syringe is exposed to environmental contaminants and which are subsequently transferred to the medicament when the syringe is introduced again in the s medicament vial for a new application.

Likewise, when a new dose of medication will be applied, commonly the vial is kept open while the patient is prepared or while the syringe is prepared to be introduced, which also promotes contamination of the medicament by its exposure to contaminants in the environment.

On the other hand, the syringes for oral dispensing of medicament commonly use pistons or plungers which has a coating made of rubber or elastomer of a flexible material on the head or tip to generate a vacuum within the syringe body and to carry out the suction of the medicament; however, due to the flexible nature of such coatings, the syringe that contains them, does not present a high precision for dispensing medicament, which results in the application of improper dosages of medicament to the patient and thereby in an altering of the required time for the recovering of the patient.

Additionally, as mentioned above, the main problem with the syringes known in the prior art, is the proper storage of the same when are not in use to avoid their contamination due to the exposure to pollutants means, since most of the syringes are only accompanied by a cellophane or plastic envelope which after opening is discarded.

OBJECTS OF THE INVENTION

It is therefore an object of this invention to provide a high precision system for dispensing medicament without spilling it or contamination, by the use a dispensing syringe specially adapted to be used in combination with an inverted adapter which is introduced and fixed in a tight manner in the mouth or neck of the vial when said vial is uncovered by the first time.

Another object of the invention is to provide a high precision syringe for dispensing medicament, which does not require the use of a coating of rubber, elastomeric or other flexible material over the piston head to provide a vacuum effect within the syringe body.

It is still a further object of the present invention to provide a piston head completely circular and designed in the level of thousandths of a millimeter that allows through that said piston run smoothly the entire inner wall of the syringe without losing tightness, without leaving residues in the inner wall of the syringe.

Another object of the invention is to provide a medicament dispensing system comprising a protective housing or hood of the dispensing syringe which protects the syringe from contamination and eliminates the use of any other container for storage said syringe when is not in use.

In addition, an object of the invention is to provide a protective housing of said syringe which can be used to place the medicament name or brand of the pharmaceutical company that produces it.

BRIEF DESCRIPTION OF THE INVENTION

These and other objects are achieved by a medicament dispensing system comprising in combination, a dispensing syringe and an inverted adapter wherein the dispensing syringe comprises a cylindrical syringe body, which has an inner surface which is completely smooth and straight, said dispensing syringe further comprises a plunger which is manufactured integrally as an only one piece, which has a piston head completely circular and flat which is designed and finished in a level of thousandths of millimeter to run the whole inner surface of the syringe without losing tightness, sliding smoothly and without leaving residues in the inner wall of the syringe.

Additionally, below the piston head, said plunger comprises four ridges orthogonally arranged in a equidistantly manner over the same, wherein the front ends or tips of said ridges matches with the outer diameter of the plunger head, said front ends have the function of preventing the oscillation or pitching of the plunger, whereby ensuring the tight seal of the tip relative to the smooth inner surface when the medicament is extracted and thus preventing the loss of vacuum.

On the other hand, the inverted adapter comprises a through hole in the center thereof for introducing the dispensing/suction pivot of the syringe, said through hole has a propeller shaped reinforcement around thereof, which reinforces the base of said hole to prevent movement of the adapter and the spillage or medicament at the moment of introducing the dispensing/suction pivot and extracting the medicament. Likewise, said propeller reinforcement prevents breakage of said adapter by introducing the pivot in a sudden movement, and also reinforces the outer wall of the adapter by inserting and fixing it into the mouth of the vial.

The outer wall of the adapter has a substantially conical shape to facilitate introduction and tight housing of the same in the mouth of the vial and prevent an easy extraction thereof, as well as the spillage of the medicament when the vial is placed in an inverted manner for the extraction of the medicament.

Said adapter further comprises a lip or edge that serves as a stop to prevent the adapter is fully inserted into the vial and provides equally an additional seal of the cap in the mouth of the vial to prevent the entering of air and the medicament contamination, as well as the spillage thereof. In its inner part, the adapter comprises a taper, which facilitates the full drainage of the medicament.

The medicament dispensing system of the present invention further comprises a housing or protective hood comprising two rings on the inner surface thereof, which are adjacent to the base to be engaged with two complementary flanges of said syringe and provide a tight engagement of said housing with the syringe.

Said housing comprises on its upper end a bullet shaped portion, which is specially adapted to receive the inverted adapter before use, or in case said adapter is not used by the user due to the mouth of the vial has a configuration completely irregular or different to that of the adapter.

With said configuration of the housing of the present invention it is provided a unique housing to contain both the syringe and adapter and in case that said syringe and adapter are opened from its package and it is decided not to use them, they can be saved for a later use in a sterile and safe manner.

The additional features and advantages of the invention should be more clearly understood by the detailed description of the preferred embodiment thereof, given by way of non-limiting example with reference to the accompanying drawings, in which:

DETAILED DESCRIPTION OF THE INVENTION

Figure 1:
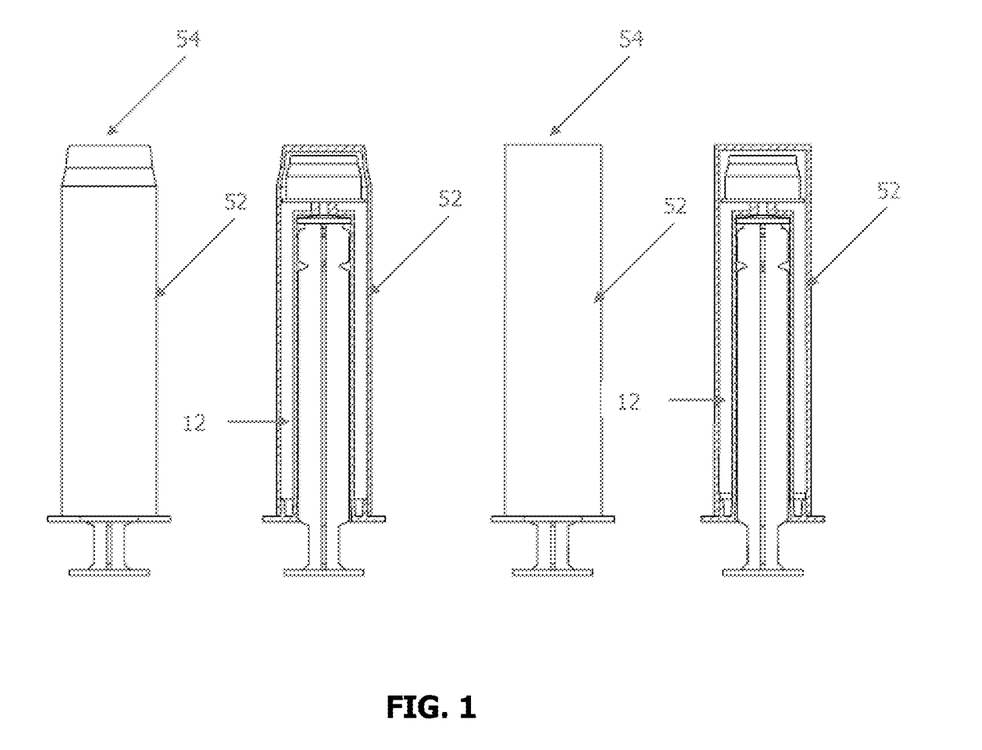
FIG. 1 shows a series of views in front plan and cross-sectional of the medicament dispensing system of the present invention.
Figure 2:
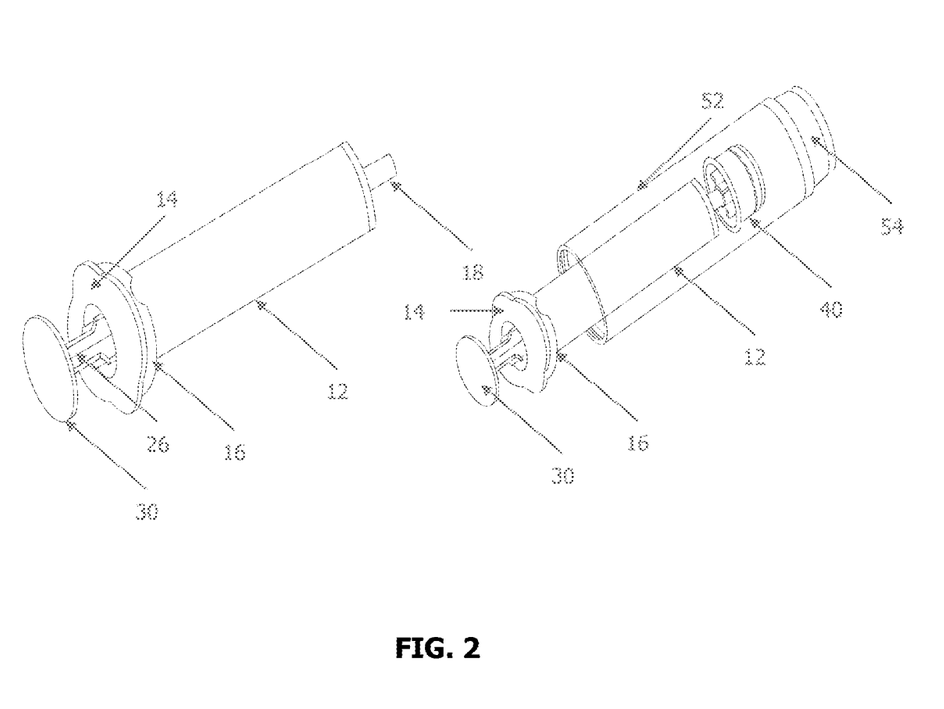
FIG. 2 shows perspective views of the medicament dispensing system of the present invention.

Referring to FIGS. 1 and 2, it is illustrated the preferred embodiment of the medicament dispensing system shown generally at 10. The medicament dispensing system 10 is mainly conformed by three main components: a syringe 12 for extraction of medicament, an adapter 40 to be tightly inserted into the medicament container and serve as an airtight inner cap thereof so as to avoid the spillage of the medicament and its contamination due to an exposure to environment and serve as a guide for the syringe 12; and a housing or hood 52 for containing and storing in a sterile manner within the same the syringe 12 and the adapter 40.

Figure 3:
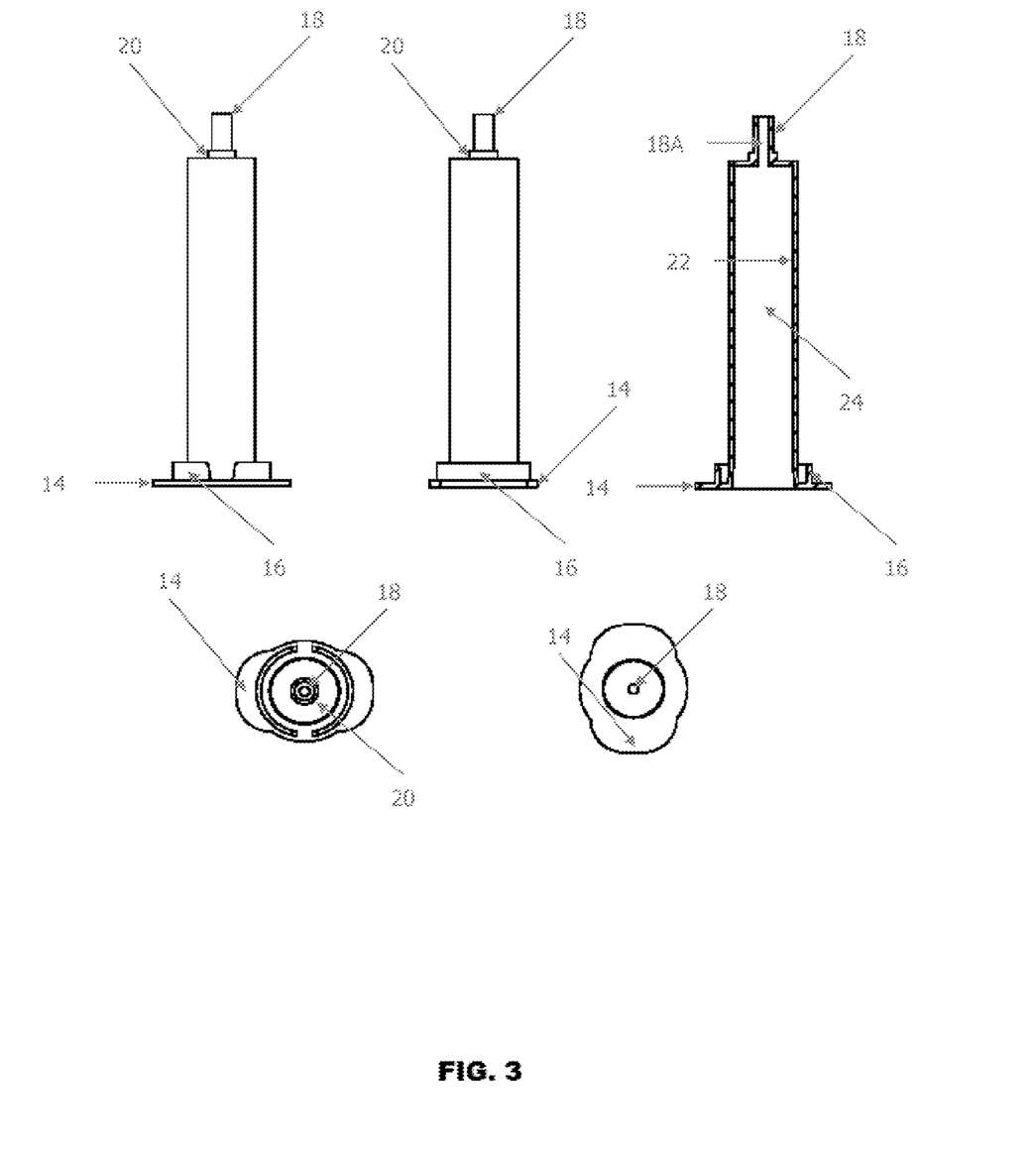
FIG. 3 illustrates a series of views in plan and cross-sectional of the syringe body and the syringe components of the medicament dispensing system of the present invention.

Referring now to FIG. 3, the syringe 12 is illustrated which comprises a syringe body 12 having a cylindrical shape, which comprises at its lower end a base 14 having a substantially circular shape which has two lateral lugs to provide a better manipulation of the syringe when is used. Said syringe further comprises two peripheral flanges or rims 16 having a substantially "U" shape which extend vertically from said base 14 and are spaced apart from each other at a predetermined distance and which almost completely surround the cylindrical syringe body 12. Said syringe comprises at its upper end a dispensing/suction pivot 18 which extends from the upper surface of said syringe body 12, from a pivot base 20. Said pivot 18 comprises a dispensing/suction conduit 18A which extends inwardly along the entire length of the pivot 18 and the pivot base 20, and which is in fluid communication with the interior of the syringe body 12, which corresponds to the vacuum chamber 24 of the syringe. Said pivot base 20 serves as a stop to limit the insertion of the pivot 18 into the adapter 40 so that the upper surface of the syringe body 12 is never in contact with the adapter 40 and much less with the medicament container 60, and to provide an additional reinforcement to said pivot 18.

The syringe body 12 further comprises an inner surface 22, which is completely straight and smooth to a mirror-polished degree, so as to provide a precise stroke or advance to the piston 26 of the medicament dispensing system of the present invention.

Figure 4:
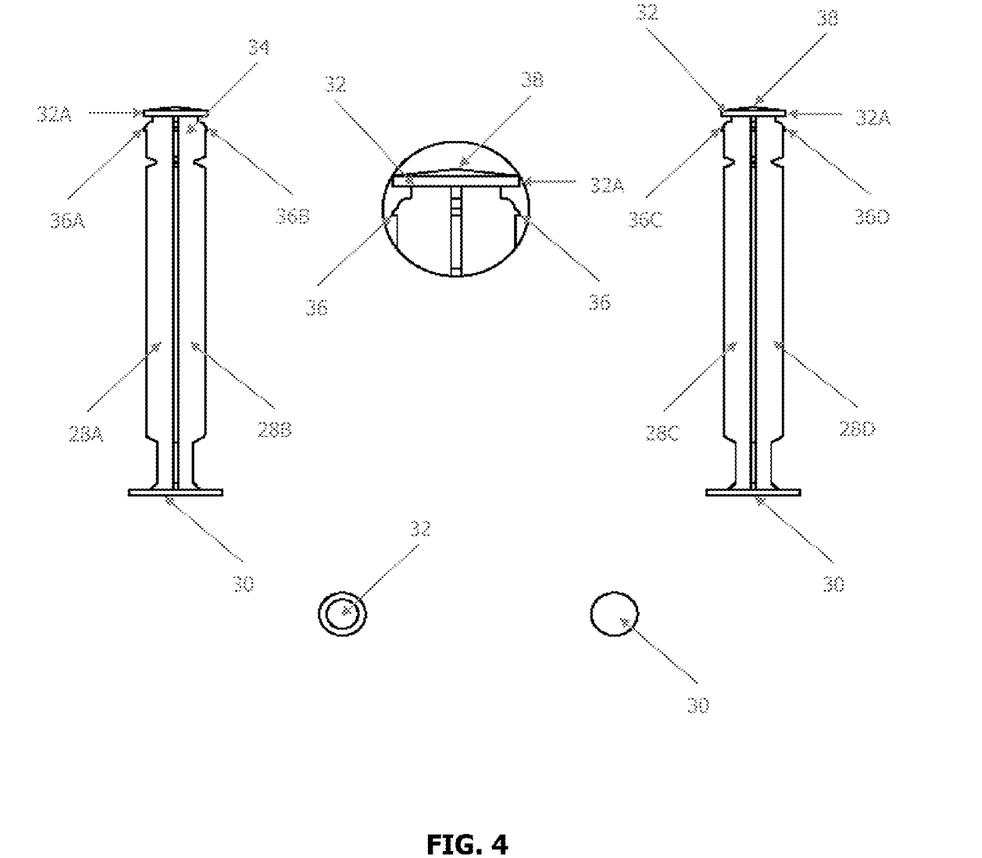
FIG. 4 shows a series of views of the piston and the syringe components of the medicament dispensing system of the present invention.

Referring to FIG. 4, the piston 26 is shown, which comprises a long and straight piston body, which is composed by a first plate and a second plate which are integrally interspersed to form a cross, so that said piston or plunger is substantially formed by four fins or vanes 28A, 28B, 28C and 28D. Said piston 26 comprises at its lower end a circular base 30 which serves as a support element to pull the piston 26 and generate a vacuum within the vacuum chamber 24 of the syringe 12. At the end where said base 30 is located, the piston comprises a portion of its length in which the plates forming said piston have a height which is smaller than the rest of said length, said portion of reduced height has the function of providing a larger contact surface in the base 30 for the support of the fingers when the suction is made to generate said vacuum in the vacuum chamber 24, so that said piston is pulled in an easy, safe and uniform manner.

At its upper end, said piston 26 comprises a piston head 32, which has a completely circular or round shape and has a conical upper surface 38, said circular head 32 has a diameter that is greater than the height of the fins 28A-28D and which is slightly greater in the range of thousandths of a millimeter than the inner diameter of cylindrical syringe body 12 for a tight advance of said plunger head 32 on the polished inner surface of the syringe body 12. Said head piston 32 is designed for a high precision fit in thousandths of a millimeter with the inner surface of the syringe body, due to its high quality finishing which is also with a mirror polished formed and to generate a constant vacuum effect and an effective and more accurate suction of medicament, without the need of using a coating of rubber, elastomer or any other flexible material, on the piston head to provide said vacuum effect within the vacuum chamber, which reduces manufacturing costs and provides an accurate or precise syringe which can be assembled in series. In this sense, the piston head 32 has a thickness with a such a dimension that the outer edge 32A of said head has a contact surface with a precision in thousandths of a millimeter for the dispensing of medicament and so as to run the entire inner surface of the syringe without losing tightness throughout the cylindrical body 12, sliding smoothly and without leaving residues on the internal wall of the syringe.

Under the piston head 32, said plunger or piston 26 comprises a segmented portion 34, said segmented portion 34 comprises in each fin 28A-28D a ridge 36, each ridge 36 of each vane 28A-28D is orthogonally arranged equidistant from each other, said ridges are located in a centered or offset manner to the head on the length of each fin of said segmented portion. The front ends or tips of said ridges 36 are coincident with the outer diameter of the piston head 32, in order to form a double support point to prevent oscillation or pitching of the piston 26, thereby ensuring the hermetic seal the head with respect to the smooth inner surface when the medicament is extracted, thereby preventing the loss of vacuum and providing a high precision syringe.

Figure 5:
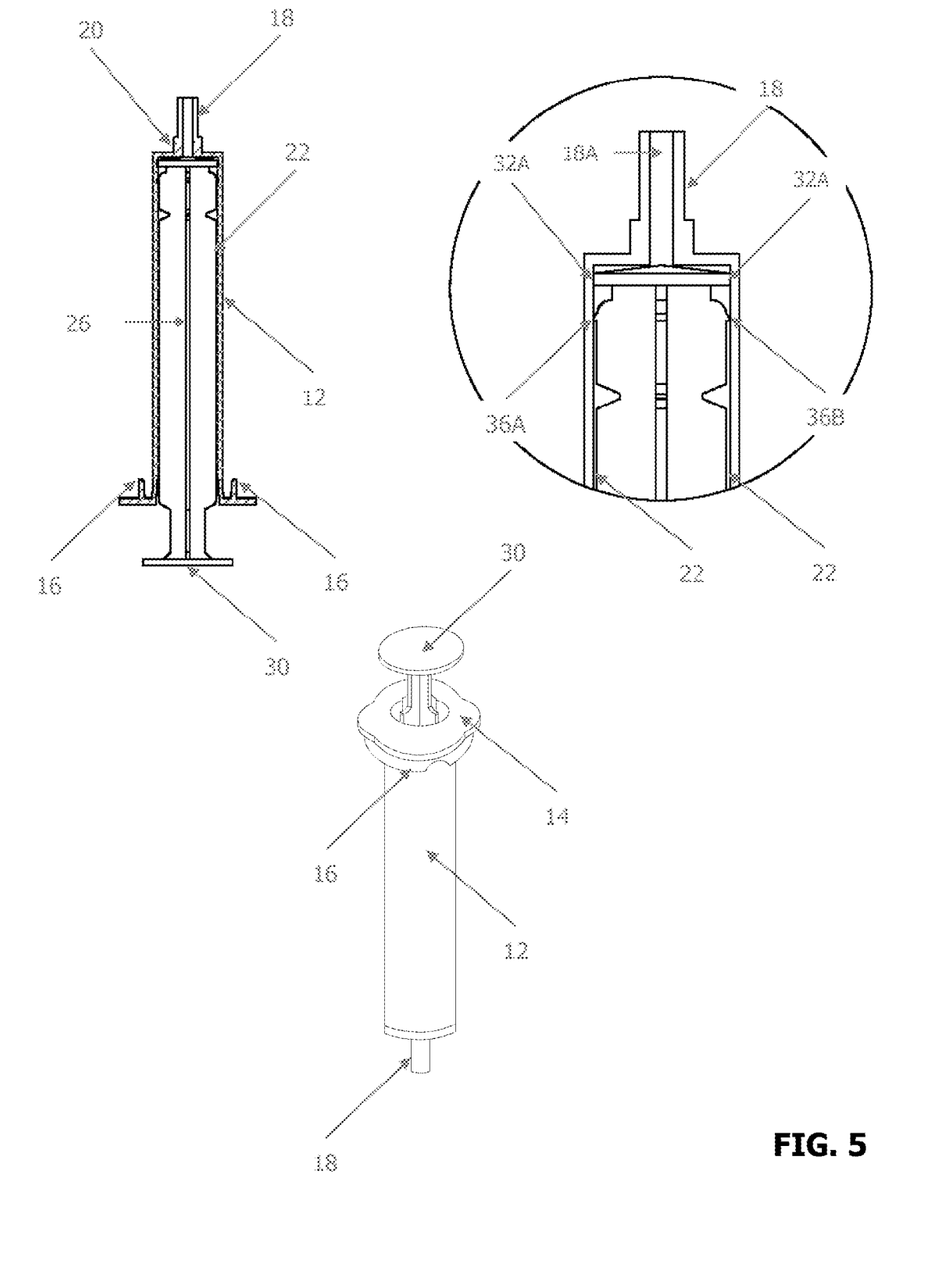
FIG. 5 shows a series of views in front plan and cross-sectional of the medicament dispensing system of the present invention wherein it is clearly appreciated the piston inserted into the syringe body.

Referring now to FIG. 5 it can be appreciated the precision coupling between the piston 26 and the syringe body 12 to form the high precision syringe of the present invention. In this sense, in said FIG. 5 is clearly shown how, both the piston head 32 and the ends 36 are in contact with the smooth interior surface of the syringe body 12 to prevent the oscillation or pitching of the piston or plunger 26.

Figure 6:
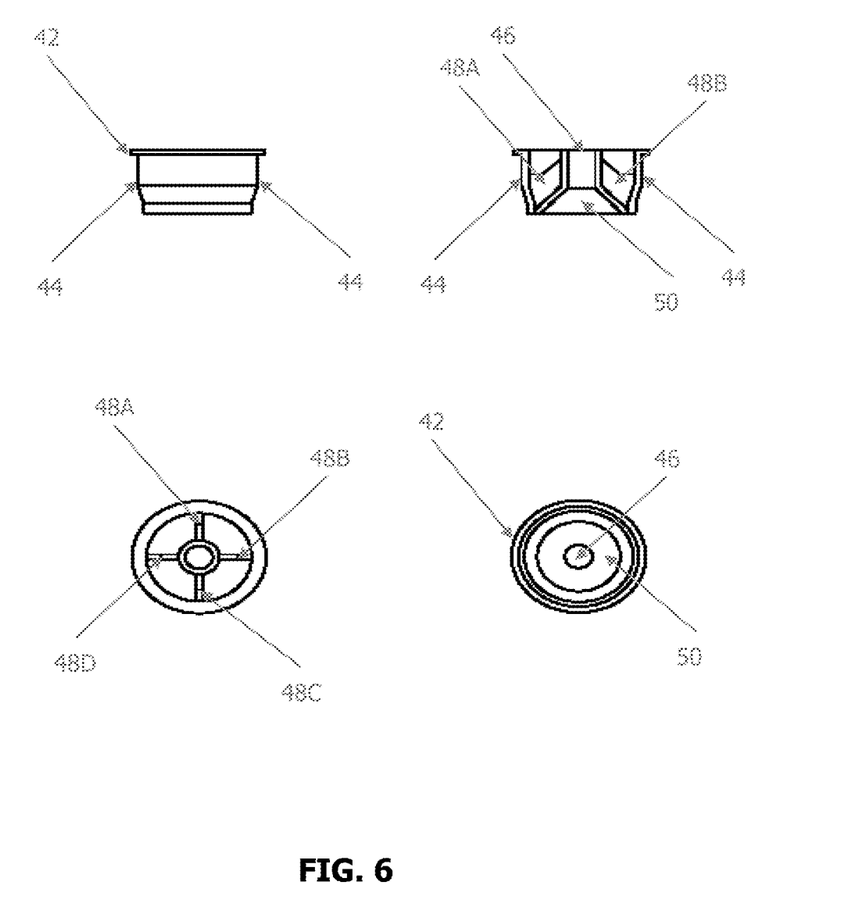
FIG. 6 shows a series of views in front plan and cross-sectional of the inverted or adapter medicament dispensing system of the present invention as well as its different components.
Figure 10:
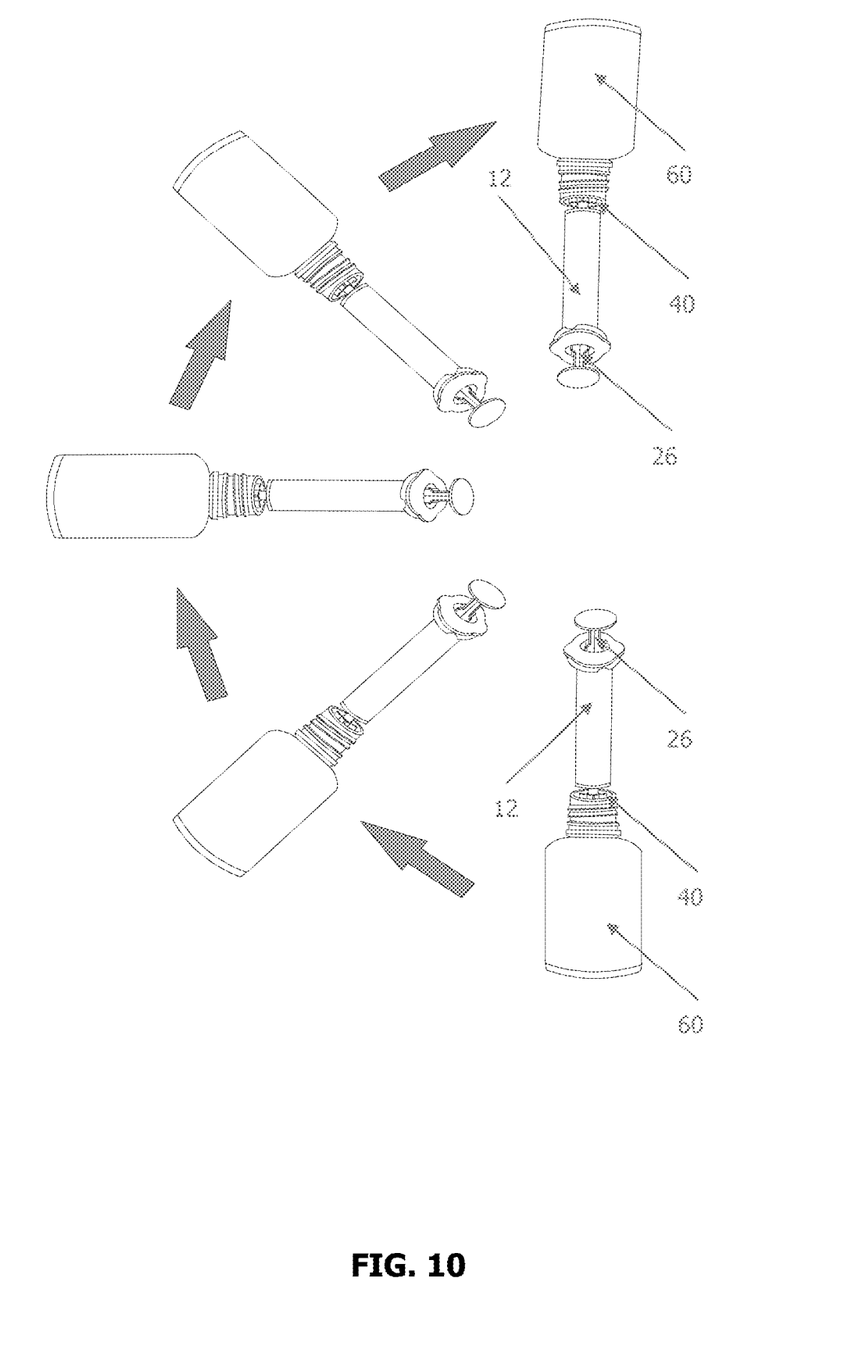
FIG. 10 shows a series of views in perspective wherein it is appreciated the syringe inserted in the medicament container from its initial position to its final position for extraction of the medicament.

FIG. 6 shows the adapter 40 in an inverted orientation, said adapter comprises a substantially cylindrical body, wherein the outer wall of said adapter 40 has a portion substantially conical or with a gradually reduced diameter, to facilitate the insertion, housing and fit of said adapter 40 on the inner surface 62 of the container or medicament vial 60. Said adapter further comprises a lip or edge 42, which serves as a stop to prevent the adapter 40 is fully inserted into the medicament vial and at the same time provides an additional seal into the mouth of the vial or container to prevent the entry of air and the contamination of the medicament by environmental exposure as well as the spillage thereof. In the lower interior part of said adapter 40, it is arranged an inverted cone 50, which serves to facilitate the emptying of the medicament when the vial 60 is in the final inverted position in order that said medicament is sucked by the syringe 12, as shown in FIG. 10.

Likewise, said adapter comprises a through hole 46 which extends from the upper surface thereof until the inverted cone 50, said through hole 46 is located in the center of the adapter 40 and has the function of receiving the pivot 18 of the syringe for the medicament suction when vacuum is generated in the vacuum chamber 24 when the piston head 32 is pulled down through the base 30 of the piston 26.

Said central hole has four propeller shaped reinforcements 48 which are orthogonally arranged thereabout, said reinforcements 48 extend from said through hole 46 until the outer wall 44 of said adapter, providing additional support to the base of said hole, to avoid movement of the adapter 40 and the spillage of the medicament when the dispensing/suction pivot 18 is inserted, so as to extract said medicament. Similarly, said propeller reinforcements prevent breaking of said adapter by introducing the pivot with a sudden movement, and also reinforce the outer wall 44 of adapter 40 when is inserted into the mouth of the vial 60. In an alternative embodiment the through hole 46 may have more than four reinforcements, for example six or eight reinforcements.

Figure 7:
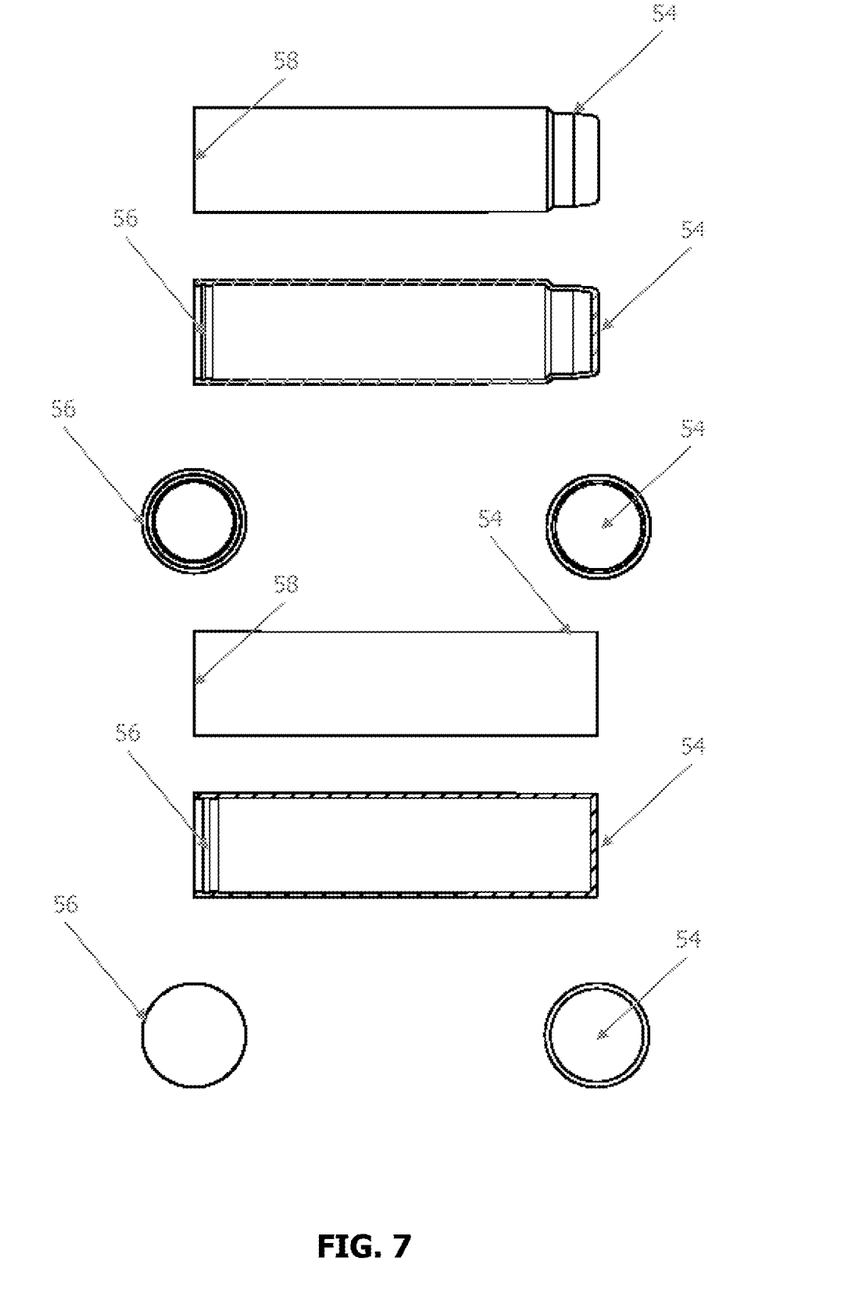
FIG. 7 shows a series of views in front plan and cross-sectional of the housing or hood of the medicament dispensing system of the present invention.

FIG. 7 illustrates a housing or hood 52, which has a substantially cylindrical shape, said housing 52 comprises at its upper end a bullet shaped portion 54, which is specially adapted to receive the adapter 40 before use, or in case said adapter is not used by the user, due to the mouth of the vial contains its own inverted or adapter or due to the mouth of the vial has a configuration completely irregular or different to that of the adapter 40, and a base 58 located at its lower end, said housing further comprises two rings 56 located in the inner surface thereof and adjacent to said base.

Figure 8:
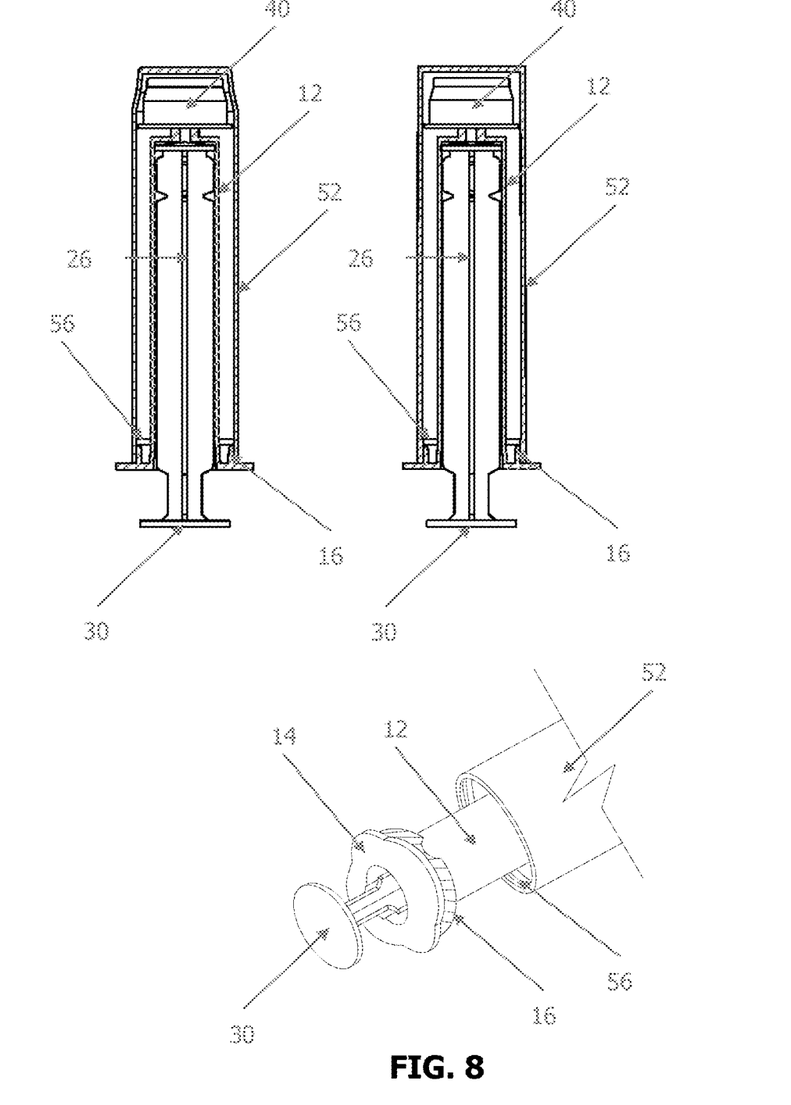
FIG. 8 shows views in perspective and cross sectional of the coupling between the syringe and the housing or hood of the medicament dispensing system of the present invention.

Said rings 56 has the function of engaging the peripheral flanges or rims 16 of the syringe by a click type system (a ridge and slot coupling), to house and retain in a secure and tight manner the syringe and adapter within said housing, as shown in FIGS. 1 and 2, when are not in use. Said click type system can be seen in FIG. 8, wherein the coupling of the flanges 16 with the rings 56 to retain the hood over the syringe. In a further embodiment, said housing can be omitted, wherein instead of said housing it is provided a wrapper made of cellophane or a similar material, in case the medicament dispensing system is used once.

Figure 9:
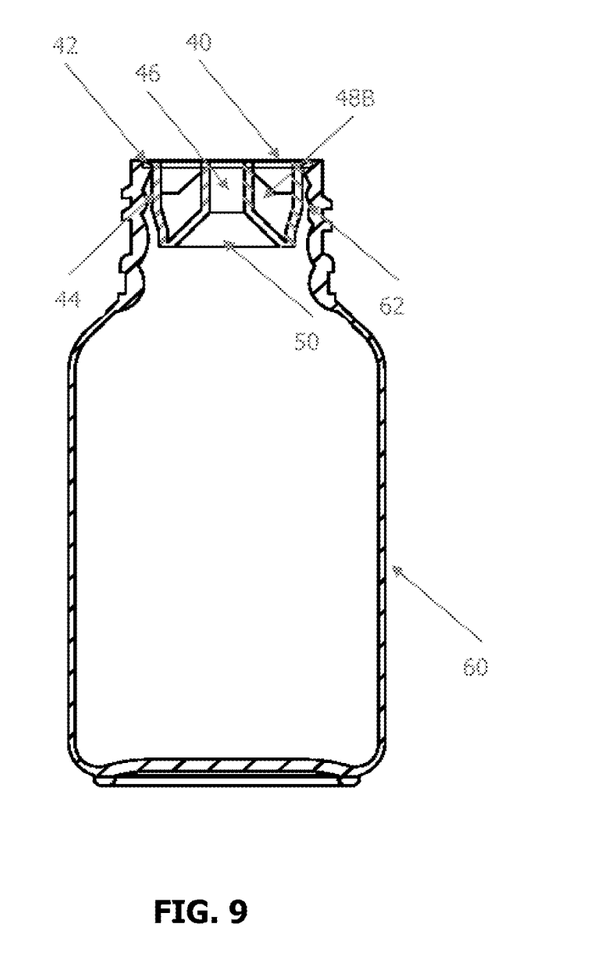
FIG. 9 shows a cross-sectional view of the adapter or inverted of the s medicament dispensing system of the present invention inserted into the medicament container.

Referring now to FIGS. 9 and 10, the operation of the medicament dispensing system of the present invention will be explained. With respect to FIG. 9 the adapter 40 inserted in a tight manner in the inner surface 62 of the vial 60 is shown, once said vial 60 has been opened for the first time. Subsequently, once inserted the adapter 60 into the vial and retained therein by means of stop 42, the syringe 12 is inserted into the through hole 46 of the adapter 40 by means of the pivot 18 until the base of the pivot contacts the upper surface of the adapter 40.

Subsequently, once the pivot 18 is inserted in the hole 46, the vial 60 is placed in an inverted position as shown in FIG. 10, once in this position, the plunger or piston 26 is pulled down by means of the base 30 the piston which causes the piston head 32 is displaced downwardly generating a vacuum in the vacuum chamber 24, causing the suction of the medicament without spillage, since the pivot is inserted in a tight manner into the hole 46. Likewise, the emptying of the medicament is promoted in a more optimal way due to the inverted cone 50, which causes that the entire medicament is extracted from the vial without any wasting and without any exposure of the medicament to the environmental pollutants. Sucking operation is maintained until the desired dose of medicament for its final application to the mouth of a patient.

Figure 11:
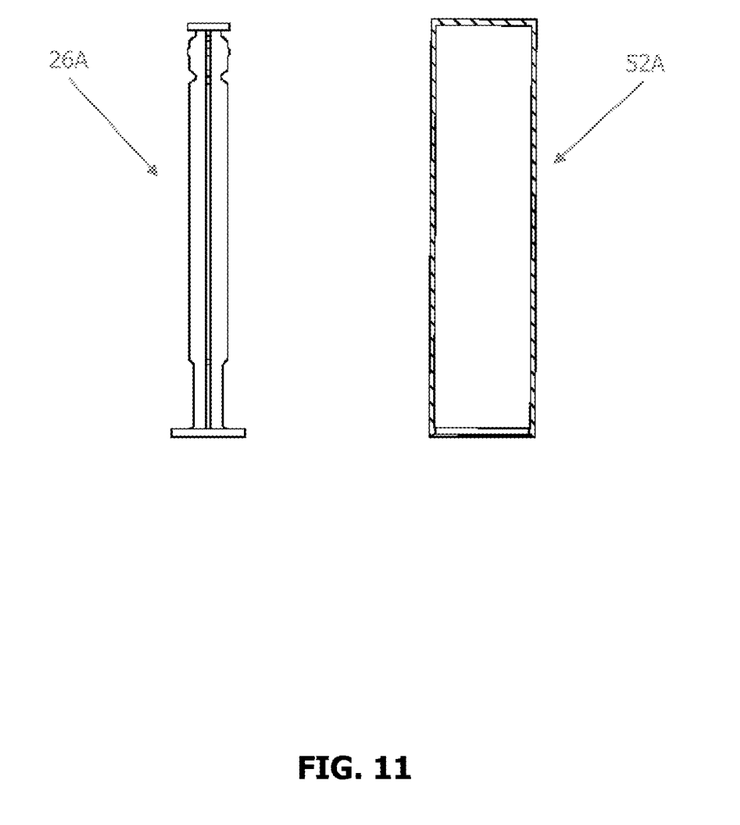
FIG. 11 is a front plan view of an alternative embodiment of the piston 26A and housing or hood 52A of the medicament dispensing system of the present invention.

FIG. 11 shows an alternative embodiment of the plunger and the housing of the medicament dispensing system, wherein the upper surface of the piston head is completely flat and the housing or hood is fully cylindrical.

Naturally, the invention as conceived may be subject to numerous modifications and variations, without drawing away from the scope of the same inventive concepts which characterize it as claimed below.

The invention claimed is:
1. A medicament dispensing system comprising:
a syringe comprising a cylindrical syringe body, which comprises at its lower end a base, a pair of lugs extending laterally outwardly from said base, and a pair of substantially peripheral U-shaped flanges which extend vertically from said base and which almost completely surround said cylindrical syringe body;

a dispensing/suction pivot at the upper end of said syringe body, which extends vertically from a pivot base located at the center of said upper surface, wherein said dispensing/suction pivot defines a dispensing/suction conduit which extends inwardly therethrough and which is in fluid communication with an inner vacuum chamber of said syringe body;

wherein said syringe further comprises a piston formed by a plurality of vanes radially equidistantly separated from each other to form a single body, said piston comprising at its lower end a circular base and a portion wherein each of said plurality of vanes has a reduced radial size near circular base, and at its upper end a circular piston head which has a diameter slightly greater than an inner diameter of said cylindrical syringe body in the range of thousandths of a millimeter, said piston head defining a conical upper surface and at its outer edge a surface which is straight and smooth to a mirror-polished degree, so as to be in contact with a straight and smooth inner surface of said cylindrical syringe body;

an adapter having a substantially cylindrical shape with a portion of its outer wall having a gradually reduced diameter to facilitate insertion in a tight manner into a vial containing medicament; said adapter defining a hole through its center which is reinforced by a plurality of propeller shaped reinforcements radially disposed between said hole and said outer wall, an inverted cone which is disposed at the inner lower end of said adapter to promote the entire emptying of the medicament when said adapter is inserted in said vial, and a lip located at the outer upper end of said adapter, which serves as a stop to prevent said adapter from being fully inserted into said vial; wherein said hole is adapted to receive said dispensing suction pivot of said syringe so as to carry out the medicament suction; and wherein each of said plurality of vanes further comprises one or more ridges disposed along a segmented portion of each of said plurality of vanes near said piston head, wherein an outer edge of each of said one or more ridges coincides with said outer edge of said piston head in order to form a double support point for said piston and to minimize oscillation or pitching of said piston during use, and wherein said piston head facilitates a desired vacuum effect into said vacuum chamber for suction of said medicament without requiring on said piston head a coating of flexible material.

2. The medicament dispensing system according to claim 1, wherein said system further comprises a housing or hood having a substantially cylindrical shape, and which can be coupled with said syringe to contain said syringe and said adapter.

3. The medicament dispensing system according to claim 2, wherein said hosing comprises two rings located along an inner surface of said housing near a housing base; wherein said rings are designed to be coupled with one or more peripheral flanges of said syringe by a click type ridge and slot coupling system.

4. The medicament dispensing system according to claim 2 or 3, wherein said housing further comprises at its upper end a bullet shaped portion which is specifically designed to house said adapter.

5. The medicament dispensing system according to claim 1, wherein said plurality of vanes is four.

6. The medicament dispensing system according to claim 1, wherein said plurality of vanes is six or eight.

7. The medicament dispensing system according to claim 1, wherein an outer diameter of said dispensing/suction pivot is slightly greater than an inner diameter of said hole in said adapter in order to facilitate a tight fit between said pivot and said hole.

8. The medicament dispensing system according to claim 1, wherein said syringe is a high precision syringe, because said piston head and an inner surface of said cylindrical syringe body are finished with a precision of thousandths of a millimeter.

9. The medicament dispensing system according to claim 1, wherein each of said one or more ridges is located offset toward said piston head along the length of each of said plurality of vanes of said segmented portion.

10. The medicament dispensing system according to claim 1, wherein said piston head defines a flat upper surface.

11. The medicament dispensing system according to claim 1, wherein the suction of said medicament is carried out by locating said vial of medicament and said syringe in an inverted manner.

12. The medicament dispensing system according to claim 11, wherein said suction is carried out by pulling downwardly said piston so that the displacement of said piston head and said one or more ridges over an inner surface of said cylindrical syringe body generates said vacuum effect causing said suction.

13. The medicament dispensing system according to claim 1, wherein said lip of said adapter provides an additional seal across a mouth of said medicament vial so as to prevent the entry of air and the contamination of said medicament by environmental exposure, and to prevent spillage of said medicament after use.

* * * * *